United States Patent [19]

Telschow

[11] Patent Number: 4,764,634
[45] Date of Patent: Aug. 16, 1988

[54] PREPARATION OF ORGANIC PHOSPHINITES

[75] Inventor: Jeffrey E. Telschow, Tarrytown, N.Y.

[73] Assignee: Akzo America Inc., New York, N.Y.

[21] Appl. No.: 900,948

[22] Filed: Aug. 27, 1986

Related U.S. Application Data

[63] Continuation-in-part of Ser. No. 816,538, Jan. 6, 1986.

[51] Int. Cl.[4] ............................................... C07F 9/46
[52] U.S. Cl. ............................................................ 558/96
[58] Field of Search ............................................ 558/96

[56] References Cited

U.S. PATENT DOCUMENTS 3,057,904 10/1962 Reetz et al. .......................... 558/96

FOREIGN PATENT DOCUMENTS 1088955  9/1960  Fed. Rep. of Germany ........ 558/96
1257153 12/1967  Fed. Rep. of Germany .
 866566  4/1961  United Kingdom .

OTHER PUBLICATIONS

Arbuzov et al., "Chem. Abs.", vol. 48 (1954), 7540G.

Primary Examiner—Anton H. Sutto
Attorney, Agent, or Firm—Richard P. Fennelly; Francis W. Young; Louis A. Morris

[57] ABSTRACT

The instant invention is directed to a process for producing organic phosphinites by a process wherein a disubstituted halophosphine is reacted with a primary, secondary, or tertiary alcohol or phenol in the presence of a tertiary amine base wherein the reaction is conducted at a temperature of from about ambient. The invention is particularly directed to the preparation of isopropyl diphenylphosphinite.

7 Claims, No Drawings

PREPARATION OF ORGANIC PHOSPHINITES

CROSS REFERENCE TO RELATED APPLICATION

This is a continuation-in-part application of application Ser. No. 816,538 filed Jan. 6, 1986.

BACKGROUND OF THE INVENTION

1. Field of the Invention

The invention is directed to the preparation of organic phosphinites and in particular to the preparation of isopropyl diphenylphosphinite (IDP).

2. Related Art

The synthesis of phosphinite by the alcoholysis of monohalophosphines is known in the art. As is indicated in "Organic Phosphorus Compounds" by Kosolapoff and Maier, Vol. 4, p. 473, the most satisfactory laboratory syntheses of phosphinites were obtained utilizing the above method. As is indicated in the article, the reaction is generally carried out in anhydrous ether or tetrahydrofuran in an inert atmosphere and at temperatures close to 0° C. Generally in the literature, the preparation of phosphinites has been conducted at temperatures close to 0° C. or within the range of −10° C. to 10° C. as specified above. For instance, in a paper entitled "The Preparation and Reactions of Diphenylphosphinous Chloride" by Stuebe, LeSuer and Norman appearing in the *Journal of the American Chemical Society*, Vol. 77, pages 3526–3529 (1955), there is discussed the preparation of hexyl diphenylphosphinite wherein a solution of diphenylphosphinous chloride in naphtha was reacted with n-hexyl alcohol, in pyridine and naphtha, at a temperature of 5°–10° C. The yield of the product obtained was 44%. It has previously been assumed that the phosphinic ester product is so unstable under the reaction conditions that preparation had to be conducted at temperatures close to 0° C.

SUMMARY OF THE INVENTION

It has been unexpectedly found that the preparation of organic phosphinites can be conducted at temperatures as high as about 60° C. without deleterious effect on the purity of the product formed. In the process of the invention, therefore, a primary, secondary or tertiary alcohol or phenol is reacted with a disubstituted halophosphine in the presence of a tertiary amine base at from about ambient temperatures to produce alkyl phosphinites in good yields.

DETAILED DESCRIPTION OF THE INVENTION

The invention is directed to the preparation of alkyl or aryl phosphinites of the formula $R^1R^2POR^3$, where $R^1$, $R^2$ and $R^3$ can be the same or different and can be alkyl, alkaryl, aryl or aralkyl containing from 1 to 30 carbon atoms. In the synthesis of the phosphinite esters by the alcoholysis of disubstituted monohalophosphine, the reaction is conducted in the presence of a tertiary amine at ambient temperatures. Ambient temperatures generally comprise from about 20° C. to 35° C. Temperatures of from about 25° C. to about 60° C. are generally acceptable, and temperatures of from about 45° C. to 55° C. are preferable.

Disubstituted monohalophosphines which can be utilized in the process of the invention comprise diethyl phosphinous chloride, diphenylphosphinous chloride, methylphenylphosphinous chloride and the like. Diphenylphosphinous chloride (DPC) is the preferred monohalophosphine for practicing the invention.

The alcohols suitable for use in the practice of the invention can comprise methanol, ethanol, isopropyl alcohol, t-butyl alcohol, phenol or generally alcohols and phenols from $C_1$ to $C_{30}$.

Tertiary amine bases that can be utilized in the process of the invention can comprise trialkylamines such as triethylamine, heteroaromatic amines such as pyridine, substituted pyridines, quinoline and the like. In the practice of the invention it is preferable to use a tertiary amine such as triethylamine.

The invention can in general comprise the reaction of stoichiometric amounts of the disubstituted halophosphine and the alcohol or phenol in the presence of a tertiary amine base. The alcohol or phenol can be and is preferably used in excess. For instance, up to 2 equivalents of alcohol is desirable while 1.2 equivalents or 20% over stoichiometry is preferable. The amount of base utilized in the practice of the invention can range from about 1.0 (stoichiometry) to about 2.0 equivalents and preferably from about 1.0 to about 1.2 equivalents.

The reaction is conducted from about ambient (25° C.) temperature to about 60° C. with stirring under nitrogen or other means to remove any source of oxygen or water from the system (which is oxidatively and hydrolytically unstable). A temperature for the reaction of from 45° C. to 55° C. is preferred to obtain a product of increased purity. The reaction mixture obtained is generally in the form of a thick slurry which is filtered or otherwise separated from the solvents to obtain the product. For recovery of the product it is possible to concentrate the filtrate, as by evaporation under reduced pressure.

The following Examples are demonstrative of an embodiment of the invention.

In the Examples, the DPC had the following assay ($P^{31}$NMR) depending on source, plant or distilled: plant 93.7%; distilled 96.9%.

EXAMPLE 1

A 100 ml 3-necked flask fitted with a 25 ml dropping funnel, mechanical stirrer and pot thermometer was charged with 8.1 ml (6.3 g, 0.105 mole) of isopropyl alcohol, 14.7 ml (10.6 g, 0.105 mole) of triethylamine, and 60 ml of hexane. To this stirred solution under $N_2$ was added dropwise 18.0 ml (22.0 g, 0.10 mole) of distilled diphenylphosphinous chloride (DPC). The reaction temperature was allowed to reach 55° C. and then was maintained at 55° C.±5° C. for the remainder (under these conditions generally from about 20 to 50 minutes, depending on the efficiency of the cooling) of the addition by means of a cold water bath.

The resulting thick slurry was stirred at ambient temperature (23°–55° C.) for one hour after the DPC addition. The mixture was filtered, the solid was washed with 50 ml of hexane, and the clear filtrate was concentrated under reduced pressure to leave 17.5 g (71.7% yield based on the amount of DPC used) of yellow isopropyl diphenylphosphinite having a 95.6% purity.

EXAMPLES 2–4

The procedure of Example 1, above, was repeated three times using the same quantities of reactants specified therein. The reactions were, however, conducted at a temperature of 25° C. for 1 hour and for 20 hours. The results are as shown. The assay was in mole % by $P^{31}$NMR.

| Conditions Crude Yield* DPC Source P Species | 25°, 1 hr 77.9% Dist. | 25°, 1 hr 82.4% Plant | 25°, 20 hr 68.9% Dist. |
|---|---|---|---|
| $(C_6H_5)_2POCH(CH_3)_2$ | 85.5 | 86.1 | 87.7 |
| $(C_6H_5)_2P(O)OCH(CH_3)_2$ | 5.9 | 5.2 | 2.8 |
| $(C_6H_5)_2P(O)H$ | 1.7 | 2.1 | 1.6 |
| $(C_6H_5)_2PCl$ | N.D. | N.D. | N.D. |
| $P(OR)_3$ | 5.2 | 3.8 | 5.1 |
| Other | 1.6 | 2.5 | 2.7 |

*Yield is based on assumption of 100% purity for both DPC and IDP.

What is claimed is:

1. A process for preparing phosphinites of the formula $R^1R^2POR^3$, wherein $R^1$, $R^2$, and $R^3$ are the same or different and can be alkyl, aryl, alkaryl, or aralkyl containing from 1 to 30 carbon atoms and wherein the reaction consists essentially of reacting a disubstituted halophosphine with an alcohol or phenol in the presence of a tertiary amine base and wherein the reaction is conducted at from about ambient temperature to about 60° C.

2. A process for preparing phosphinites consisting essentially of reacting a disubstituted halophosphine with an alcohol or phenol in the presence of a tertiary amine base and wherein the reaction is conducted at from about ambient temperature to about 60° C.

3. The process of claim 2 wherein the disubstituted halophosphine is diphenylphosphinous chloride.

4. The process of claim 2 wherein the alcohol is isopropyl alcohol.

5. The process of claim 2 wherein the tertiary amine is triethylamine.

6. The process of claim 2 wherein the reaction is conducted at a temperature of from about 45° C. to about 55° C.

7. The process of claim 1 wherein the temperature of reaction ranges from about 20° C. to about 60° C.

* * * * *